(12) United States Patent
Bruna

(10) Patent No.: US 8,267,086 B2
(45) Date of Patent: Sep. 18, 2012

(54) FLUID PRODUCT DISPENSING DEVICE WITH DOSE INDICATOR

(75) Inventor: Pascal Bruna, Sotteville les Rouen (FR)

(73) Assignee: Valois SAS, Le Neubourg (FR)

( * ) Notice: Subject to any disclaimer, the term of this patent is extended or adjusted under 35 U.S.C. 154(b) by 2127 days.

(21) Appl. No.: 10/532,961

(22) PCT Filed: Oct. 24, 2003

(86) PCT No.: PCT/FR03/03155
§ 371 (c)(1),
(2), (4) Date: Apr. 27, 2005

(87) PCT Pub. No.: WO2004/039443
PCT Pub. Date: May 13, 2004

(65) Prior Publication Data
US 2005/0284471 A1    Dec. 29, 2005

(30) Foreign Application Priority Data

Oct. 28, 2002  (FR) .................................... 02 13472

(51) Int. Cl.
*A62B 7/00* (2006.01)
*A62B 9/00* (2006.01)
*A61M 11/00* (2006.01)

(52) U.S. Cl. .......... 128/205.23; 128/200.14; 128/200.23

(58) Field of Classification Search ............. 128/200.14, 128/200.22–200.24, 203.12, 203.15, 203.23, 128/205.23; 377/6, 13, 15–16; 222/504, 222/162

See application file for complete search history.

(56) References Cited

U.S. PATENT DOCUMENTS

| 5,544,647 | A | | 8/1996 | Jewett et al. |
| 5,564,414 | A | * | 10/1996 | Walker et al. ............. 128/200.23 |
| 5,755,218 | A | * | 5/1998 | Johansson et al. ........ 128/200.14 |
| 5,895,159 | A | * | 4/1999 | Liou .................................. 401/2 |
| 6,029,659 | A | | 2/2000 | O'Connor |
| 6,327,017 | B2 | * | 12/2001 | Barberi et al. ................. 349/177 |
| 2004/0097873 | A1 | * | 5/2004 | Langley et al. .................. 604/67 |
| 2006/0289008 | A1 | * | 12/2006 | Rand et al. ................ 128/203.15 |

FOREIGN PATENT DOCUMENTS

| DE | 43 40 593 A | 6/1994 |
| EP | 0 684 047 A | 11/1995 |
| WO | WO 02 058771 A | 8/2002 |

* cited by examiner

*Primary Examiner* — Kristen Matter
(74) *Attorney, Agent, or Firm* — Sughrue Mion, PLLC

(57) ABSTRACT

A fluid dispenser device including: a body (1) incorporating a dispenser orifice (5); a reservoir (10) containing the fluid; and a dispenser member (15), such as a metering valve or pump, for selectively dispensing the fluid contained in the reservoir (10), the device also including a dose indicator having an electronic display the display including a permanent display member (21) that does not require any energy in order to keep the display unchanged, and that requires only a small amount of energy in order to change the display.

20 Claims, 3 Drawing Sheets

000
FLUID PRODUCT DISPENSING DEVICE WITH DOSE INDICATOR

FIELD OF THE INVENTION

The present invention relates to a fluid dispenser device, and more particularly to such a device incorporating a dose indicator.

BACKGROUND

It is well known to use dose indicators, and more particularly dose counters, with fluid dispenser devices. The term "fluid" refers to gases, liquids, pastes, or powders. The counters are generally for displaying the number of doses that have been dispensed or the number of doses that remain to be dispensed, and various types of counters have been made. A first family of counters is constituted by mechanical devices that generally include counting wheels that are turned while the device is being actuated. Such counters present drawbacks in that they are generally rather bulky and require the structure of the device to be modified significantly so as to enable the counter to be adapted thereto. In addition, since the size of such counters is limited, the number of doses that can be counted is clearly also limited, and when a large number of doses is disposed in the reservoir, e.g. 200 doses, the display generally becomes very small and therefore difficult to read, in particular for the elderly. Another type of counter is constituted by electronic counters. Such counters include an electronic display which is changed each time the device is actuated. Such electronic counters require an electricity supply, and are generally also rather bulky. Depending on the type of energy source used, there is the risk that after a relatively long storage period, the energy source will be exhausted, such that the counter can no longer operate. In particular, this can occur with batteries, whether rechargeable or otherwise. Documents EP-684 047, U.S. Pat. No. 6,029,659, WO 02/058771, and U.S. Pat. No. 5,544,647 disclose the use of liquid crystal displays (LCDs) which require a power supply (generally by means of a battery) in order to operate.

SUMMARY OF PREFERRED EMBODIMENTS OF INVENTION

An object of the present invention is to provide a fluid dispenser device which does not have the above-mentioned drawbacks.

More particularly, an object of the present invention is to provide a fluid dispenser device including a dose indicator that is compact and that is adaptable to any type of existing fluid dispenser device without having to modify its structure or its external dimensions.

Another object of the present invention is to provide such a device enabling any number of doses to be counted in a manner that is easy to read.

Another object of the present invention is to provide such a device that is simple and inexpensive to manufacture and to assemble, and that operates in reliable manner, while requiring as little energy as possible in order to operate.

The present invention therefore provides a fluid dispenser device comprising: a body incorporating a dispenser orifice; a reservoir containing the fluid; and a dispenser member, such as a metering valve or pump, for selectively dispensing the fluid contained in the reservoir, the device further comprising a dose indicator comprising electronic display means, said display means including a permanent display member, such as a bistable nematic display member, that does not require any energy in order to keep the display unchanged, and that requires only a small amount of energy in order to change said display.

The display member is advantageously of the liquid crystal display (LCD) type.

The display member advantageously includes bistable nematic crystals.

In a first variant embodiment, the energy required to change the display is provided by a battery that may optionally be rechargeable.

In an advantageous second variant embodiment, the energy required to change the display is created while the device is being actuated.

The interaction between two portions of the device moving relative to each other while the device is being actuated, is advantageously transformed by an electromechanical converter into an electric pulse used to change the display.

Advantageously, said interaction involves one portion of the device rubbing or striking against another portion of the device during actuation.

The reservoir is advantageously displaceable relative to the body of the device during actuation, said body including a contactor co-operating with said reservoir, the interaction between said reservoir and said contactor creating the electric pulse required to change the display.

In a variant, a striker pin is displaced against a contactor while the device is being actuated, said contactor being unable to move relative to said body, and said striker pin co-operating with a spring.

Advantageously, said dose indicator indicates the number of doses of fluid that have been dispensed or that remain to be dispensed from the reservoir.

Advantageously, said dose indicator is thin in structure so that it is adaptable to a fluid dispenser device without having to modify the outside dimensions thereof.

BRIEF DESCRIPTION OF THE DRAWINGS

Other characteristics and advantages of the present invention appear more clearly from the following detailed description, given by way of non-limiting example, and with reference to the accompanying drawings, and in which.

DETAIL DESCRIPTION OF PREFERRED EMBODIMENTS OF THE INVENTION

The embodiment shown in the figures is an inhaler, generally referred to as a "Metered Dose Inhaler" (MDI). The inhaler includes a reservoir 10 containing a fluid and a propellant gas, a metering valve 15 being assembled on the reservoir 10 so as to dispense doses of fluid through a mouthpiece 5 formed in a body 1 which receives the reservoir 10. The device is generally actuated by displacing the reservoir 10 axially inside the body 1, thereby actuating the valve so as to dispense a dose of fluid. At this point, it should be noted that the invention is not limited to this particular type of device, but that, on the contrary, the invention is adaptable to any type of fluid dispenser device, and in particular to devices including pumps, rather than valves operating with a propellant gas.

Figure 1:
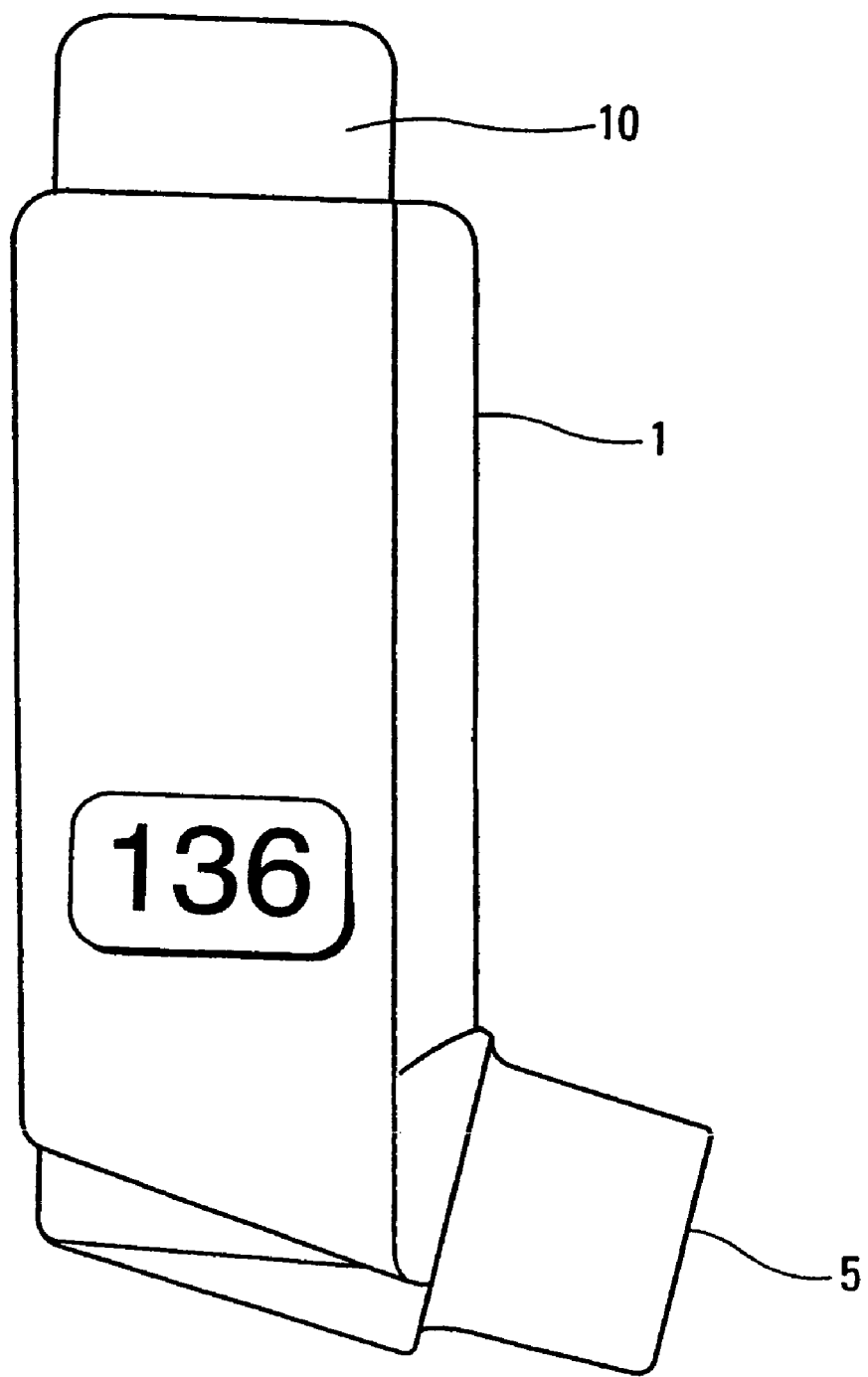
FIG. 1 is a very diagrammatic side view showing a fluid dispenser device constituting an embodiment of the present invention.

In the invention, the device includes a dose indicator. The indicator is preferably used to count the number of doses that have been dispensed or that remain to be dispensed from the reservoir 10. The indicator includes electronic display means 20 that are preferably large in size, as shown in FIG. 1. This enables everyone, even the elderly having impaired vision, to read the number displayed by the display means 20, even when the number of doses is very high, and the counter is designed to count several hundred doses.

In the invention, the display means 20 include a permanent or remanent display member 21. The permanent display member 21 can be of the LCD type, e.g. a display member having bistable nematic crystals. A permanent or remanent display member does not require any energy in order to keep the display unchanged, so that between two actuations, no energy source is required for the number displayed by the display means to remain visible to the user. Such display means therefore differ from traditional liquid crystal displays which operate only with a power supply, generally a battery. It is only when the display needs to be changed, i.e. while the device is being actuated, that a very small amount of energy is required in order to change said display. This very small amount of energy can be supplied by an optionally-rechargeable battery. Preferably, however, and as described below, it can be created while the device is being actuated, and hence no battery is required.

In the preferred embodiment, in which the indicator operates without a battery, the energy required in order to change the display can be created by the interaction between two portions of the device that move relative to each other during actuation. The interaction, which can involve one portion rubbing or striking against another portion, for example, is then transformed into one or more electric pulses that suffice to enable the display to be changed. The interaction can advantageously be created between the reservoir 10 and a portion of the body 1 that move relative to each other during actuation.

Figure 2:
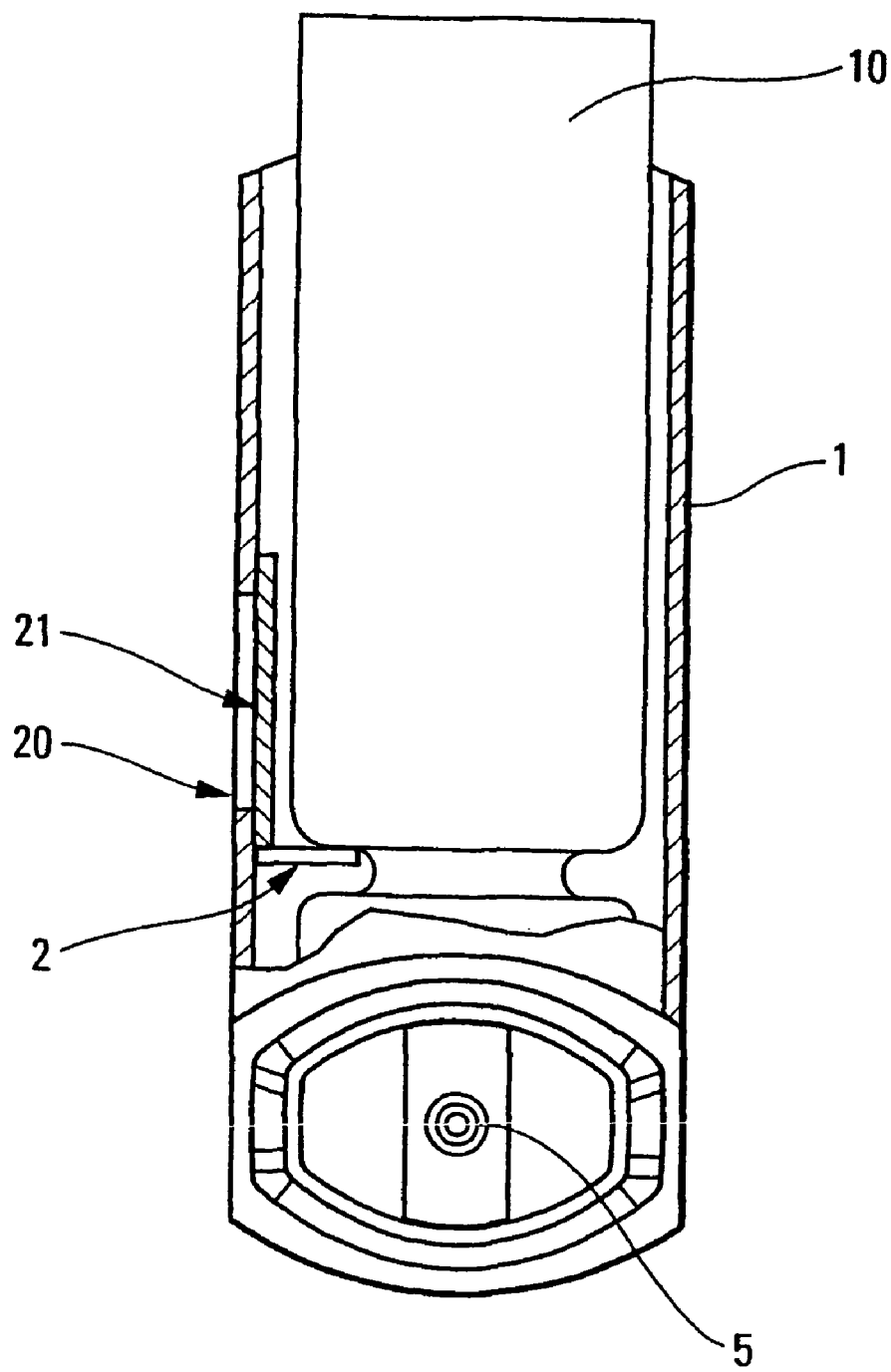
FIG. 2 is a very diagrammatic front view in section of the FIG. 1 device.

FIG. 2 shows a particular embodiment, in which a contactor 2 is secured to the reservoir 10, said contactor coming to strike the display member 21 when the reservoir 10 is returned to its rest position after dispensing a dose. Naturally, the contactor could be secured to the body 1 and co-operate with the reservoir, or more generally, friction between the reservoir and any piece held securely to the body could be sufficient to create the electric pulse required to change the number on display. The electric pulse, typically having a duration lying in the range 1 millisecond (ms) to 50 ms, and having a voltage lying in the range about 10000 volts (V) to 50000 V, is then processed by a suitable electronic circuit 25 so as to control the display member 21.

Figure 3:
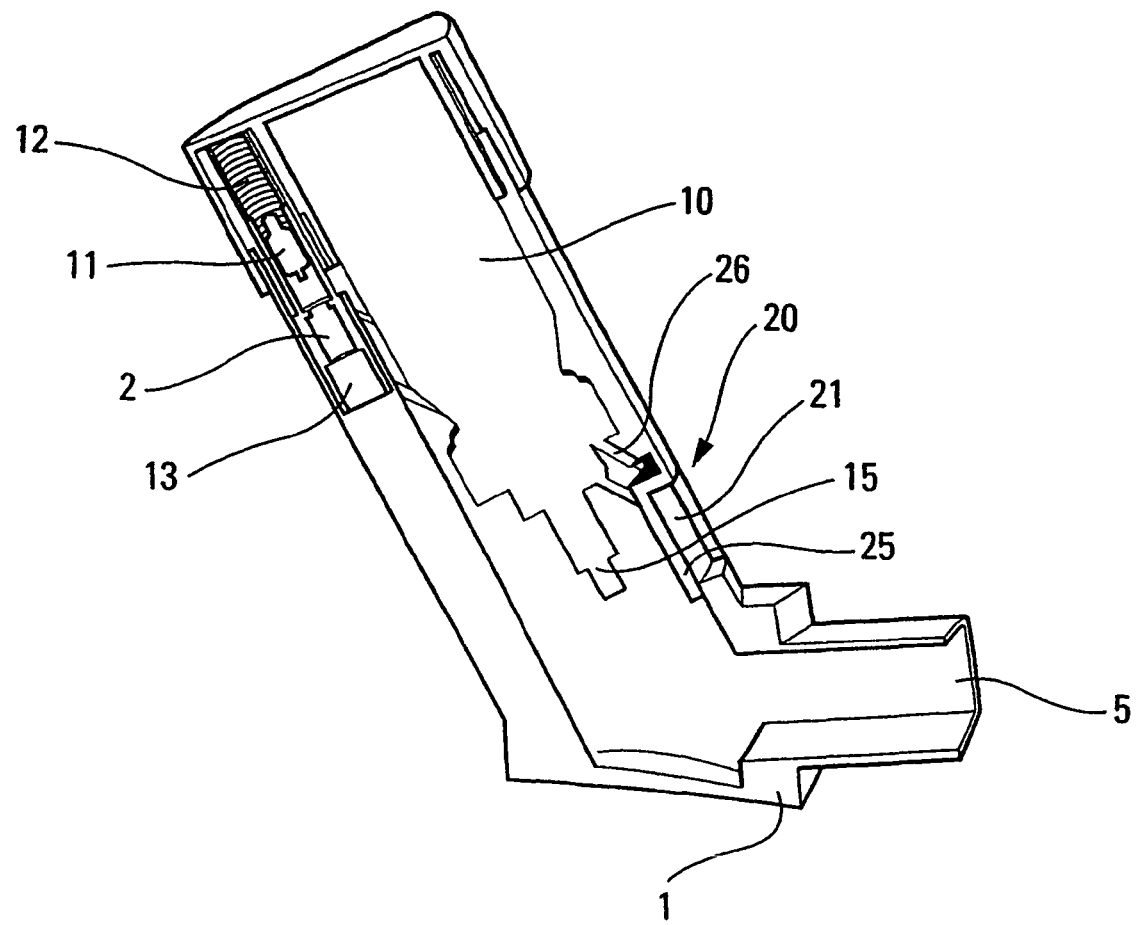
FIG. 3 is a diagrammatic side view in section of a variant embodiment of the invention.

FIG. 3 shows a variant embodiment, in which an electric-pulse generator of the flint type is used. This system includes a striker pin 11 co-operating with a spring 12 and urged against a contactor 2 during actuation. The contactor 2, advantageously includes a ceramic secured to an anvil 13, and is preferably held stationary relative to the body 1. Power supply wires 26 convey the pulse to the electronic circuit 25, which transforms it so as to control the display member 21 in order to change the display.

More generally, it is possible to envisage converting the force, or the mechanical displacement while the device is being actuated, into an electric signal. It is possible to use a piezoelectric actuator, an electromagnetic coil, or any other electromechanical-conversion device known to the person skilled in the art. More particularly, a flint-type system, or a piezoelectric ceramic such as that used in gas-lighters, could be used. Other variants can thus be envisaged. For example, a thermoelectric generator could be used, in particular to take advantage of the propellant gas expanding when a metering valve is used.

The dose indicator, which is preferably made in the form of a dose counter, can be adapted to count the number of doses that remain to be dispensed or the number of doses that have already been dispensed from the reservoir 10.

As shown in particular in FIG. 3, the display member 21 and the electronic circuit 25 of the indicator advantageously present a structure that is thin, so that it can be adapted to any dispenser device without having to modify its external dimensions. In the embodiment in FIGS. 2 and 3, the display member is merely integrated inside the body 1, behind a window, so as to enable the user to read the indications written on said display member.

Although described with reference to particular embodiments, the invention is not in any way limited to the embodiments shown, and any modifications could be applied thereto by a person skilled in the art, without going beyond the ambit of the present invention as defined by the accompanying claims.

The invention claimed is:

1. A fluid dispenser device comprising: a body (1) incorporating a dispenser orifice (5); a reservoir (10) containing the fluid; and a dispenser member (15) for selectively dispensing the fluid contained in the reservoir (10), the device being characterized in that it further comprises a dose indicator comprising electronic display means (20), said display means (20) including a permanent display member (21) that does not require any energy in order to keep the display unchanged, and that requires only a small amount of energy in order to change said display; and wherein said indicator operates without a battery; and the energy required to change the display is created while the device is being actuated during actuation of the fluid dispenser member.

2. A device according to claim 1, in which the display member (21) is of the liquid crystal display (LCD) type.

3. A device according to claim 1, in which the display member (21) includes bistable nematic crystals.

4. A device according to claim 1, in which an interaction between two portions (10, 11; 1, 2) of the device moving relative to each other while the device is being actuated, is transformed by an electromechanical converter into an electric pulse used to change the display.

5. A device according to claim 4, in which said interaction involves one portion (10, 11) of the device rubbing or striking against another portion (1, 2) of the device during actuation.

6. A device according to claim 5, in which the reservoir (10) is displaceable relative to the body (1) of the device during actuation, said body (1) including a contactor (2) co-operating with said reservoir (10), the interaction between said reservoir (10) and said contactor (2) creating the electric pulse required to change the display.

7. A device according to claim 5, in which a striker pin (11) is displaced against a contactor (2) while the device is being actuated, said contactor (2) being unable to move relative to said body (1), and said striker pin (11) co-operating with a spring (12).

8. A device according to claim 1, in which said dose indicator indicates the number of doses of fluid that have been dispensed or that remain to be dispensed from the reservoir.

9. A dispenser according to claim 1, in which said dose indicator is thin in structure so that it is adaptable to a fluid dispenser device without having to modify the outside dimensions thereof.

10. The dispenser according to claim 1, wherein the dispenser member is a metering valve or pump.

11. The device according to claim 1, wherein the energy required to change the display is created during dispensing of the fluid by the dispenser member.

12. A fluid dispenser device comprising:
a body comprising a dispenser orifice;
a reservoir comprising a fluid; and
a dispenser member that selectively dispenses the fluid from the reservoir; and
a dose indicator comprising an electronic display, the display comprising a permanent display member that does not require energy to keep the display unchanged and that requires electrical energy to change the display; and
wherein the electrical energy required to change the display is generated during actuation of the fluid dispenser member by interaction between two physical portions of the device moving relative to each other.

13. The device according to claim 12, wherein the electrical energy required to change the display is generated by interaction between two physical portions of the device moving relative to each other while the device is being actuated.

14. The device according to claim 12, wherein the electrical energy required to change the display is generated without a battery.

15. The device according to claim 12, wherein the display is a liquid crystal display (LCD).

16. The device according to claim 12, wherein the display comprises bistable nematic crystals.

17. The device according to claim 12, wherein the interaction between two physical portions of the device moving relative to each other involves one portion of the device rubbing or striking against another portion of the device during actuation.

18. The device according to claim 12, wherein the reservoir is displaceable relative to the body of the device during actuation, the body comprising a contactor co-operating with the reservoir, the interaction between the reservoir and the contactor generating the electric energy required to change the display.

19. The device according to claim 12, comprising a striker pin and a contactor, wherein the striker pin is displaced against the contactor while the device is actuated, the contactor unable to move relative to the body and said striker pin co-operating with a spring.

20. The device according to claim 12, wherein the electrical energy required to change the display is generated during dispensing of the fluid by the dispenser member.

* * * * *